(12) United States Patent
Ito et al.

(10) Patent No.: US 8,093,422 B2
(45) Date of Patent: *Jan. 10, 2012

(54) METHOD FOR DEUTERATION OF AN AROMATIC RING

(75) Inventors: Nobuhiro Ito, Kawagoe (JP); Tsuneaki Maesawa, Kawagoe (JP); Kazushige Muto, Kawagoe (JP); Kosaku Hirota, Gifu (JP); Hironao Sajiki, Gifu (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 530 days.

This patent is subject to a terminal disclaimer.

(21) Appl. No.: 10/521,531

(22) PCT Filed: Jul. 10, 2003

(86) PCT No.: PCT/JP03/08783

§ 371 (c)(1),
(2), (4) Date: Feb. 22, 2007

(87) PCT Pub. No.: WO2004/011400

PCT Pub. Date: May 2, 2004

(65) Prior Publication Data

US 2007/0255076 A1    Nov. 1, 2007

(30) Foreign Application Priority Data

Jul. 26, 2002    (JP) .................. 2002-219005

(51) Int. Cl.
*C07C 63/04*    (2006.01)
*C07C 39/28*    (2006.01)
*C07C 13/00*    (2006.01)

(52) U.S. Cl. ........................ 562/493; 568/774; 585/24

(58) Field of Classification Search .............. 568/27, 568/58; 585/269, 270

See application file for complete search history.

(56) References Cited

U.S. PATENT DOCUMENTS

| | | | |
|---|---|---|---|
| 3,849,458 A | 11/1974 | Dinh-Nguyen et al. | |
| 4,591,626 A | 5/1986 | Kawai et al. | |
| 4,874,890 A | 10/1989 | Kato et al. | |
| 4,880,941 A | 11/1989 | Shroot et al. | |
| 5,221,768 A | 6/1993 | Kato et al. | |
| 5,830,763 A * | 11/1998 | Junk et al. | 436/56 |
| 6,794,522 B2 * | 9/2004 | Bergman et al. | 549/429 |
| 2005/0177015 A1 | 8/2005 | Hirota et al. | |
| 2006/0025596 A1 | 2/2006 | Ito et al. | |
| 2006/0116535 A1 | 6/2006 | Ito et al. | |

FOREIGN PATENT DOCUMENTS

| | | | |
|---|---|---|---|
| EP | 0 276 675 | | 8/1988 |
| EP | 1 535 889 | | 6/2005 |
| GB | 1103607 | * | 2/1968 |
| GB | 1103607 | * | 2/1988 |
| JP | 47-12567 | | 6/1972 |
| JP | 45-17402 | | 6/1976 |
| JP | 60-248666 | | 12/1985 |
| JP | 61-275241 | | 12/1986 |
| JP | 61-277648 | | 12/1986 |
| JP | 62-56441 | | 3/1987 |
| JP | 63-30435 | | 2/1988 |
| JP | 63-30450 | | 2/1988 |
| JP | 63-198638 | | 8/1988 |
| JP | 5-19536 | | 3/1993 |
| JP | 6-228014 | | 8/1994 |
| JP | 06228014 | * | 8/1994 |
| WO | 2003/104166 | | 12/2003 |
| WO | 2004/011400 | | 2/2004 |
| WO | 2004/046066 | | 6/2004 |

OTHER PUBLICATIONS

Uno et al., Infrared spectra of benzene- and pentadeuterobenzenesulfonyl compounds, Spectrochimica Acta, Part A: Molecular and Biomolecular Spectroscopy (1968), 24(11), 1705-12. (Abstract).*
Wszolek et al., Skeletal rearrangements in mass spectra. I. Bis-aryl compounds, Organic Mass Spectrometry (1968), 1(1), 127-37. (Abstract).*
Usov et al., Highly Mobile Solvent Holes in Viscous Squalane Solutions As Detected by Quantum Beats and Mary Spectroscopy Techniques, Journal of Physical Chemistry A (1999), 103(11), 1690 (Abstract).*
Sokol'skii et al., Selectivity during hydrogenation of phenylacetylene on metallic catalysts, Khimicheskaya (1987), (5), 32-35 (Abstract).*
Tsuzuki et al., Syntheses of phenol derivatives labeled with deuterium, Journal of Deuterium Science (1993), 3(1), 28-32 (Abstract).*
Junk et al., Preparative supercritical deuterium exchange in arenes and heteroarenes, Tetrahedron letters, 37, 201996, 3445-3448.*
Junk et al. (1), {Preparative supercritical deuterium exchange in arenes and heteroarenes, Tetrahedron letters, 37, 201996, 3445-3448}.*
Hsiao et al., {Preparation of Fully Deuterated Fatty Acids by Simple Method, American Oil Chemists' Society, Chicago, 1994, 9(11), 913-915}.*

(Continued)

*Primary Examiner* — Paul A Zucker
(74) *Attorney, Agent, or Firm* — Hamre, Schumann, Mueller & Larson, P.C.

(57) ABSTRACT

The present invention relates to a method for deuteration of a compound having an aromatic ring, using an activated catalyst, and the method comprises reacting a compound having an aromatic ring with heavy hydrogen source in the presence of an activated catalyst selected from a platinum catalyst, a rhodium catalyst, a ruthenium catalyst, a nickel catalyst and a cobalt catalyst.

6 Claims, No Drawings

OTHER PUBLICATIONS

Garnett et al., {Catalytic deuterium exchange reactions with aromatics. VI. Platinum catalyst reproducibility and activation procedures, Journal of Catalysis (1963), 2(4), 339-347}.*

Fraser et al, Journal of the American Chemical Society, The Steric Effect in the Platinum-catalyzed Exchange Reaction Between Aromatic Ring Protons and Deuterium Oxide, 1966, 88(19), pp. 4365-4370.

Kirk-Othmer, Encyclopedia of Chemical Technology, 4th Edition, 1993, vol. 5, pp. 383-389.

Baker et al., "Aromatic Reactivity. Part XX. Diphenyl Sulphide, Dibenzofuran, and Dibenzothiophen in Detritiation", Chemical Abstracts (1961); 56: 5077-5081.

Werstiuk et al., "The High Temperature and Dilute Acid (HTDA) Procedure as a General Method of Replacing Aromatic Hydrogen by Deuterium. II", Canadian Journal of Chemistry (1974); 52: 2169-2171.

Junk et al., "Preparative Supercritical Deuterium Exchange in Arenes and Heteroarenes", Tetrahedron Letters (1996); 37: 3445-3448.

Usov et al., "Determination of a Fraction of Spin-Correlated Radical Ion Pairs in Irradiated Alkanes by Quantum Oscillation Technique", Radiation Physics and Chemistry (1997); 49: 237-243.

Klei et al., "Iridium-Catalyzed H/D Exchange into Organic Compounds in Water", J. Am. Chem. Soc., vol. 24, No. 10, 2002, pp. 2092-2093.

Sajiki et al., "Pd/C-H2-Catalysed Deuterium exchange reaction of the benzylic site in D20", Synlett, No. 7, Jul. 1, 2002, pp. 1149-1151.

Hardacre et al., "A highly efficient synthetic procedure for deuteriating imidazoles and imidazolium salts", Chem. Commun., 2001, pp. 367-368.

Oba et al., "Biosynthesis of luciferin in the sea firefly, *Cypridina hilgendorfii*: L-tryptophan is a component in Cypridina luciferin", Tetrahedron Letters 43 (2002) 2389-2392.

Junk et al., "Hydrogen isotope exchange reactions involving C-H (D,T) bonds", Chemical Society Reviews, 1997, vol. 26, pp. 401-406.

Garnett et al., "An NMR study of orientation effects in the catalytic deuteration and tritiation of aromatic compounds. Simplification of spin-coupled NMR spectra by the method of massive deuteration," Tetrahedron Letters, vol. 2, 1961, pp. 516-522.

Elvidge et al., "tirtiun nuclear magnetic resonance spectroscopy. Par 10. Distribution of Tritium in some labeled nitrogen heterocyclic compounds", J. Chem. Soc. Perkin Transactions 2, 1979, pp. 386-388.

Kiuru et al. "Deuteration of Estrogens using Pd/C as a Catalyst" Synthesis and Applications of Isotopically Labelled Compounds 1997: Proceedings of the Sixth International Symposium, Philadelphia, USA, Sep. 14-18, 1997, (1998) pp. 475-477.

Hardacre, C. et al., "A highly efficient synthetic procedure for deuteriating imidazoles and imidazolium salts," Chem. Commun., 2001, p. 367-368.

Hirota, K. And Ueda, T., "Differences in the Catalytic Activity of Nickel, Platinum and Palladium as Observed in the Isotopic Exchange Reaction of Paraxylene with Deuterium Oxide," Bull. Chem. Soc. Japan, 1962, vol. 35, No, 2, p. 228-232,.

Kalpala, J. et al., "Deuteration of 2-methylnaphthalene and eugenol in supercritical and pressurized hot deuterium oxide," Green Chemistry, 2003, vol. 5, p. 670-676.

Rubottom, G.M. And Evain, E.J., "Deuteration of Pyridine Derivatives: A Very Mild Procedure," Tetrahedron, 1990, vol, 46, No. 15, p. 5055-5064.

Sajiki, H. et al., "Efficient C-H/C-D Exchange Reaction on the Alkyl Side Chain of Aromatic Compounds Using Heterogeneous Pd/C in $D_2O$," Organic Letters, 2004, vol. 6, No. 9, p. 1485-1487.

Search report for international application No. PCMP03/14182, dated Jan. 13, 2004 (4 pages).

Search report for international application No. PCT/JP03/14181, dated Jan. 13, 2004 (2 pages).

Search report for international application No. PCT/JP2004/019049, dated Feb. 22, 2005 (2 pages).

Search report for European application No. 04807406.6, dated Jul. 16, 2007 (2 pages).

Garnett et al., "Deuterium Exchange Reactions with Substituted Aromatics, II. The Monohalogenated Benzenes and Naphthalenes," Aust. J. Chem., vol. 14 (1961), p. 441-448.

Garnett, J.L. and Sollich, W.A., "Catalytic Deuterium Exchange Reactions with Aromatics VI. Studies in Platinum Catalyst Reproducibility and Activation Procedures," Journal of Catalysis, v, 2, p. 339-347 (1963).

Cristol, S. J. et al,, "Bridged polycyclic compounds. XX. Cis stereochemistry of the addition of methanol and water to endo-trimethylenenorbomene," Tetrahedron Letters (1963), p. 185-9 (abstract).

* cited by examiner

METHOD FOR DEUTERATION OF AN AROMATIC RING

TECHNICAL FIELD

The present invention relates to a method for deuteration of a compound having an aromatic ring, using an activated catalyst.

BACKGROUND OF THE INVENTION

A compound having a heavy hydrogen (deuterium and tritium) is said to be useful in various purposes. For example, a deuterated compound is very useful in clarification of reaction mechanism and substance metabolism and used widely as a labeled compound. Said compound is also known to be useful as drugs, pesticides, organic EL materials, and the like due to change in stability and property itself by isotope effect thereof. A compound having tritium also is said to be useful as a labeled compound in animal tests and the like to survey absorption, distribution, concentration in blood, secretion, metabolism and the like of drugs, etc. Therefore, research on a compound having a heavy hydrogen (deuterium and tritium) has been increasing also in these fields.

Various methods for obtaining these compounds having a heavy hydrogen have conventionally been used, however, there are many problems to be solved in deuteration technology of an aromatic ring, among others, and it was difficult to efficiently and industrially obtain a compound having a deuterated aromatic ring.

Conventional technology includes a method for deuteration of an aromatic compound under high temperature condition using heavy water and hydrochloric acid (Can. J. Chem. 1974, 52, 2169, etc.), a method for deuteration of an aromatic compound under basic condition using supercritical $D_2O$ (Tetrahedron Letters 1996, 37, 3445, etc.), a method for deuteration of an aromatic compound having a hydrophilic group under basic condition using a catalyst (JP-A-62-56441, etc.), a method for deuteration of an aromatic compound at high temperature using a non-activated catalyst (JP-A-63-198638, etc.), a method for deuteration of an organic compound under basic condition using heavy hydrogen peroxide (U.S. Pat. No. 3,849,458, etc.), a method for deuteration of a halogen atom once introduced to an aromatic compound (JP-A-6-228014, etc.), etc.

However, a deuteration method containing the addition process of an acid or a base to a reaction system is not only impossible to deuterate an aromatic compound labile to decomposition under acidic or basic condition but also has a problem that a substrate to be deuterated is limited to only an aromatic compound having a hydrophilic functional group.

Further, a modified method using heavy hydrogen peroxide, which was developed to provide deuteration of an aromatic compound having no hydrophilic functional group, cannot deuterate a compound labile to decomposition by heavy hydrogen peroxide, and further said method cannot deuterate an aromatic compound labile to decomposition by alkaline substance, which is essential to be added to a reaction system.

Furthermore, in a conventional deuteration method carried out under acidic or basic condition, complicated purification processes are required in isolation of thus deuterated compound, because reaction solution is not neutral, even if a compound not labile to decomposition under acidic or basic condition is used as a substrate.

Further, a method for deuteration under high temperature condition is difficult to be applied to a compound labile to decomposition at high temperature and a method for using supercritical $D_2O$ has a problem that a compound to be a reaction substrate tends to be decomposed due to significantly high reactivity of supercritical $D_2O$.

Furthermore, a method for halogenation once not only requires a halogenation process of a compound to be a substrate but also has a serious problem that deuteration proceeds only at moiety introduced with a halogen atom and not at an aromatic ring itself.

In view of the above situation, development of a method is needed for deuteration of an, aromatic compound efficiently and industrially irrespective of presence and non-presence of a substituent or types thereof.

SUMMARY OF THE INVENTION

The present invention relates to a method for deuteration of a compound having an aromatic ring, which comprises reacting the compound having an aromatic ring with heavy hydrogen source in the presence of an activated catalyst selected from a platinum catalyst, a rhodium catalyst, a ruthenium catalyst, a nickel catalyst and a cobalt catalyst.

Further, the present invention relates to a compound represented by the general formula [2]:

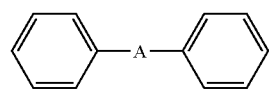

[2]

(wherein A is a sulfur atom, a sulfonyl group or a sulfinyl group and at least one of hydrogen atoms belonging to an aromatic ring is a heavy hydrogen atom).

BEST MODE FOR CARRYING OUT OF THE INVENTION

In the present invention, a heavy hydrogen means deuterium (D) and tritium (T) and deuteration means substitution with deuterium and tritium.

In a method for deuteration of the present invention, the compound having an aromatic ring may have not less than 1 hydrogen atom in the aromatic ring, and includes an aromatic ring which may have a substituent.

The aromatic ring of the aromatic ring which may have a substituent may be a monocyclic or a condensed polycyclic and in the case of a condensed polycyclic one, aromatic rings themselves or an aromatic ring and an aliphatic ring may be condensed, and such a condensed polycyclic one may be straight chained, branched or cyclic and may take plane structure or stereo structure.

When the aromatic ring has substituents, number of the substituents is generally 1 to 5, preferably 1 to 2 and more preferably 1.

Specific examples of the above aromatic ring include benzene, naphthalene, anthracene, phenanthrene, 9,10-dihydroanthracene, naphthacene, pentaphene, pentacene, hexaphene, hexacene, heptaphene, heptacene, trinaphthylene, 1,4-dihydronaphthalene, pyrene, triphenylene, biphenylene, indene, indan, indacene, phenalene, fluorene, acenaphthene, acenaphthylene, fluoranthene, tetraphenylene, coranthrene, acephenanthrylene, aceanthrylene, cyclopentaphenanthrene, chrysene, picene, pleiadene, rubicene, pyranthrene, coronene, perylene, rubrene, dibenzophenanthrene, 1,2-dibenzo-1,3-cycloheptadiene and ovalene.

Specific examples of the substituent of the aromatic ring which may have a substituent includes a halogen atom, a hydroxyl group, a mercapto group, an oxo group, a thioxo group, a carboxyl group, a sulfo group, a sulfino group, a sulfeno group, a phosphino group, a phosphinoyl group, a formyl group, an amino group, a cyano group and a nitro group, and an alkyl group, an alkenyl group, an aryl group, an aralkyl group, an alkoxy group, an aryloxy group, an alkylthio group, an arylthio group, an alkylsulfonyl group, an arylsulfonyl group, an alkylsulfinyl group, an arylsulfinyl group, an alkylphosphino group, an arylphosphino group, an alkylphosphinoyl group, an arylphosphinoyl group, an alkylamino group, an arylamino group, an alkoxycarbonyl group, an aryloxycarbonyl group, an alkoxysulfonyl group, an aryloxysulfonyl group, an acyl group and an acyloxy group, which may have further a substituent.

The above alkyl group may be straight chained, branched or cyclic, and includes one generally having 1 to 20, preferably 1 to 15, more preferably 1 to 10 and further preferably 1 to 6 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a n-heptyl group, an isoheptyl group, a sec-heptyl group, an n-octyl group, an isooctyl group, a sec-octyl group, a n-nonyl group, a n-decyl group, an n-undecyl group, a n-dodecyl group, a n-tridecyl group, a n-tetradecyl group, a n-pentadecyl group, a n-hexadecyl group, a n-heptadecyl group, an n-octadecyl group, a n-nonadecyl group, an n-icosyl group, a cyclopropyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group and a cycloicosyl group.

The alkenyl group may be straight chained, branched or cyclic, and includes one generally having 2 to 20, preferably 2 to 10 and more preferably 2 to 6 carbon atoms, and having not less than 1 carbon-carbon double bond in the chain of the above alkyl group having not less than 2 carbon atoms, among the above alkyl groups, which is specifically exemplified by a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, a 2,4-pentadienyl group, a 1,1-dimethyl-2-propenyl group, an 1-ethyl-2-propenyl group, a 1,2-dimethyl-1-propenyl group, a 1-methyl-1-butenyl group, a 5-hexenyl group, a 4-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, an 2-octenyl group, a 3-nonenyl group, a 4-decenyl group, a 1-dodecenyl group, a 1-tetradecenyl group, a 1-hexadecenyl group, an 1-octadecenyl group, a 1-icosenyl group, a 1-cyclopropenyl group, a 2-cyclopentenyl group, a 2,4-cyclopentadienyl group, a 1-cyclohexenyl group, a 2-cyclohexenyl group, a 3-cyclohexenyl group, a 2-cycloheptenyl group, a 2-cyclononenyl group, a 3-cyclodecenyl group, a 2-cyclotridecenyl group, a 1-cyclohexadecenyl group, a 1-cyclooctadecenyl group and a 1-cycloicosenyl group.

The aryl group includes one generally having 6 to 14, preferably 6 to 10 carbon atoms, which is specifically exemplified by a phenyl group, a naphthyl group and an anthryl group.

The aralkyl group may be straight chained, branched or cyclic, and includes one generally having 7 to 34, preferably 7 to 20 and more preferably 7 to 15 carbon atoms, which is the above alkyl group substituted with the above aryl group, which is specifically exemplified by a benzyl group, a phenylethyl group, a phenylpropyl group, a phenylbutyl group, a phenylpentyl group, a phenylhexyl group, a phenylheptyl group, a phenyloctyl group, a phenylnonyl group, a phenyldecyl group, a phenylundecyl group, a phenyldodecyl group, phenyltridecyl group, a phenyltetradecyl group, a phenylpentadecyl group, a phenylhexadecyl group, a phenylheptadecyl group, a phenyloctadecyl group, a phenylnonadecyl group, a phenylicosyl group, a naphthylethyl group, a naphthylpropyl group, a naphthylbutyl group, a naphthylpentyl group, a naphthylhexyl group, a naphthylheptyl group, a naphthyloctyl group, a naphthylnonyl group, a naphthyldecyl group, a naphthylundecyl group, a naphthyldodecyl group, a naphthyltridecyl group, a naphthyltetradecyl group, a naphthylpentadecyl group, a naphthylhexadecyl group, a naphthylheptadecyl group, a naphthyloctadecyl group, a naphthylnonadecyl group, a naphthylicosyl group, an anthrylethyl group, an anthrylpropyl group, an anthrylbutyl group, an anthrylpentyl group, an anthrylhexyl group, an anthrylheptyl group, an anthryloctyl group, an anthrylnonyl group, an anthryldecyl group, an anthrylundecyl group, an anthryldodecyl group, an anthryltridecyl group, an anthryltetradecyl group, an anthrylpentadecyl group, an anthrylhexadecyl group, an anthrylheptadecyl group, an anthryloctadecyl group, an anthrylnonadecyl group, an anthrylicosyl group, a phenanthrylethyl group, a phenanthrylpropyl group, a phenanthrylbutyl group, a phenanthrylpentyl group, a phenanthrylhexyl group, a phenanthrylheptyl group, a phenanthryloctyl group, a phenanthrylnonyl group, a phenanthryldecyl group, a phenanthrylundecyl group, a phenanthryldodecyl group, a phenanthryltridecyl group, a phenanthryltetradecyl group, a phenanthrylpentadecyl group, a phenanthrylhexadecyl group, a phenanthrylheptadecyl group, a phenanthryloctadecyl group, a phenanthrylnonadecyl group and a phenanthrylicosyl group.

The alkoxy group may be straight chained, branched or cyclic, and includes one generally having 1 to 20, preferably 1 to 15, more preferably 1 to 10 and further preferably 1 to 6 carbon atoms, which is specifically exemplified by a methoxy group, an ethoxy group, a propoxy group, an isopropoxy group, a butoxy group, an isobutoxy group, a sec-butoxy group, a tert-butoxy group, a pentyloxy group, a neopentyloxy group, a hexyloxy group, an isohexyloxy group, a tert-hexyloxy group, a heptyloxy group, an octyloxy group, a nonyloxy group, a decyloxy group, an undecyloxy group, a tetradecyloxy group, a hexadecyloxy group, a heptadecyloxy group, a nonadecyloxy group, an icosyloxy group, a cyclohexyloxy group, a cyclooctyloxy group, a cyclodecyloxy group and a cyclononadecyloxy group.

The aryloxy group includes one generally having 6 to 14, preferably 6 to 10 carbon atoms, which is specifically exemplified by a phenoxy group, a naphthyloxy group and an anthryloxy group.

The alkylthio group may be straight chained, branched or cyclic, and includes one generally having 1 to 20, preferably 1 to 15, more preferably 1 to 10 and further preferably 1 to 6 carbon atoms, wherein an oxygen atom in the above alkoxy group is replaced by a sulfur atom, which is specifically exemplified by a methylthio group, an ethylthio group, a propylthio group, an isopropylthio group, a butylthio group, an isobutylthio group, a tert-butylthio group, a pentylthio group, a hexylthio group, an octylthio group, a nonylthio group, a decylthio group, a tridecylthio group, a tetradecylthio group, a hexadecylthio group, an octadecylthio group, an icosylthio group, a cyclohexylthio group, a cyclodecylthio group and a cycloheptadecylthio group.

The arylthio group includes one wherein an alkyl group in the above alkylthio group is replaced by the above aryl group, which is specifically exemplified by a phenylthio group, a naphthylthio group and an anthrylthio group.

The alkylsulfonyl group may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a tert-butylsulfonyl group, a pentylsulfonyl group, a neopentylsulfonyl group, a hexylsulfonyl group, an isohexylsulfonyl group, a tert-hexylsulfonyl group, a heptylsulfonyl group, an octylsulfonyl group, a nonylsulfonyl group, a decylsulfonyl group, an undecylsulfonyl group, a tetradecylsulfonyl group, a hexadecylsulfonyl group, a heptadecylsulfonyl group, a nonadecylsulfonyl group, an icosylsulfonyl group, a cyclohexylsulfonyl group, a cyclooctylsulfonyl group, a cyclodecylsulfonyl group and a cyclononadecylsulfonyl group.

The arylsulfonyl group includes one generally having 6 to 14, preferably 6 to 10 carbon atoms, which is specifically exemplified by a phenylsulfonyl group, a naphthylsulfonyl group and an anthrylsulfonyl group.

The alkylsulfinyl group may be straight chained, branched or cyclic, and includes one generally having 1 to 20, preferably 1 to 15, more preferably 1 to 10 and further preferably 1 to 6 carbon atoms, which is specifically exemplified by a methylsulfinyl group, an ethylsulfinyl group, a n-propylsulfinyl group, an isopropyl sulfinyl group, a n-butylsulfinyl group, an isobutylsulfinyl group, a tert-butylsulfinyl group, a pentylsulfinyl group, a neopentylsulfinyl group, a hexylsulfinyl group, an isohexylsulfinyl group, a tert-hexylsulfinyl group, a heptylsulfinyl group, an octylsulfinyl group, a nonylsulfinyl group, a decylsulfinyl group, an undecylsulfinyl group, a tetradecylsulfinyl group, a hexadecylsulfinyl group, a heptadecylsulfinyl group, a nonadecylsulfinyl group, an icosylsulfinyl group, a cyclohexylsulfinyl group, a cyclooctylsulfinyl group, a cyclodecylsulfinyl group and a cyclononadecylsulfinyl group.

The arylsulfinyl group includes one, wherein the alkyl group of the above alkylsulfinyl group is replaced by the above aryl group, which is specifically exemplified by a phenylsulfinyl group, a naphthylsulfinyl group and an anthrylsulfinyl group.

The alkylphosphino group includes one, wherein one or two of hydrogen atoms of a phosphino group is independently replaced by the above alkyl group, which is specifically exemplified by a methylphosphino group, an ethylphosphino group, a n-propylphosphino group, an isopropylphosphino group, a n-butylphosphino group, an isobutylphosphino group, a tert-butylphosphino group, a pentylphosphino group, a hexylphosphino group, a heptylphosphino group, an octylphosphino group, a nonylphosphino group, a decylphosphino group, a dodecylphosphino group, a tetradecylphosphino group, a pentadecylphosphino group, a hexadecylphosphino group, a heptadecylphosphino group, a nonadecylphosphino group, an icosylphosphino group, a cyclopentylphosphino group, a cyclohexylphosphino group, a cycloheptylphosphino group, a dimethyiphosphino group, an ethylmethylphosphino group, a diethylphosphino group, a methylpropylphosphino group, a dipropylphosphino group, an ethylhexylphosphino group, a dibutylphosphino group, a heptylmethylphosphino group, a methyloctylphosphino group, a decylmethylphosphino group, a dodecylethylphosphino group, a methylpentadecylphosphino group, an ethyloctadecylphosphino group, a cyclopentylmethylphosphino group, a cyclohexylmethylphosphino group, a cyclohexylethylphosphino group, a cyclohexylpropylphosphino group, a cyclohexylbutylphosphino group and a dicyclohexylphosphino group.

The arylphosphino group includes one, wherein one or two of hydrogen atoms of a phosphino group is each independently replaced by the above aryl group, which is specifically exemplified by a phenylphosphino group, a diphenylphosphino group, a naphthylphosphino group and an anthrylphosphino group.

The alkylphosphinoyl group includes one, wherein one or two of hydrogen atoms of a phosphinoyl group is each independently replaced by the above alkyl group, which is specifically exemplified by a methylphosphinoyl group, an ethylphosphinoyl group, a n-propylphosphinoyl group, an isopropylphosphinoyl group, a n-butylphosphinoyl group, an isobutylphosphinoyl group, a tert-butylphosphinoyl group, a pentylphosphinoyl group, a hexylphosphinoyl group, a heptylphosphinoyl group, an octylphosphinoyl group, a nonylphosphinoyl group, a decylphosphinoyl group, a dodecylphosphinoyl group, a tetradecylphosphinoyl group, a pentadecylphosphinoyl group, a hexadecylphosphinoyl group, a heptadecylphosphinoyl group, a nonadecylphosphinoyl group, a icosylphosphinoyl group, a cyclopentylphosphinoyl group, a cyclohexylphosphinoyl group, a cycloheptylphosphinoyl group, a dimethylphosphinoyl group, an ethylmethylphosphinoyl group, a diethylphosphinoyl group, a methylpropylphosphinoyl group, a dipropylphosphinoyl group, an ethylhexylphosphinoyl group, a dibutylphosphinoyl group, a heptylmethylphosphinoyl group, a methyloctylphosphinoyl group, a decylmethylphosphinoyl group, a dodecylethylphosphinoyl group, a methylpentadecylphosphinoyl group, an ethyloctadecylphosphinoyl group, a cyclopentylmethylphosphinoyl group, a cyclohexylmethylphosphinoyl group, a cyclohexylethylphosphinoyl group, a cyclohexylpropylphosphinoyl group, a cyclohexylbutylphosphinoyl group and a dicyclohexylphosphinoyl group.

The arylphosphinoyl group includes one, wherein one or two of hydrogen atoms of a phosphinoyl group is replaced by the above aryl group, which is specifically exemplified by a phenylphosphinoyl group, a diphenylphosphinoyl group, a naphthylphosphinoyl group and an anthrylphophinoyl group.

The alkylamino group includes one, wherein one or two of hydrogen atoms of an amino group is each independently replaced by the above alkyl group, which is specifically exemplified by a methylamino group, an ethylamino group, a n-propylamino group, an isopropylamino group, a n-butylamino group, an isobutylamino group, a tert-butylamino group, a pentylamino group, a hexylamino group, a heptylamino group, an octylamino group, a nonylamino group, a decylamino group, a dodecylamino group, a tetradecylamino group, a pentadecylamino group, a hexadecylamino group, a heptadecylamino group, a nonadecylamino group, an icosylamino group, a cyclopentylamino group, a cyclohexylamino group, a cycloheptylamino group, a dimethylamino group, an ethylmethylamino group, a diethylamino group, a methylpropylamino group, a dipropylamino group, an ethylhexylamino group, a dibutylamino group, a heptylmethylamino group, a methyloctylamino group, a decylmethylamino group, a dodecylethylamino group, a methylpentadecylamino group, an ethyloctadecylamino group, a cyclopentylmethylamino group, a cyclohexylmethylamino group, a cyclohexylethylamino group, a cyclohexylpropylamino group, a cyclohexylbutylamino group and a dicyclohexylamino group.

The arylamino group includes one, wherein one or two of hydrogen atoms of an amino group is replaced by the above aryl group, which is specifically exemplified by a phenylamino group, a diphenylamino group, a naphthylamino group and an anthrylamino group.

The alkoxycarbonyl group may be straight chained, branched or cyclic, and includes one generally having 2 to 21 preferably 2 to 15, more preferably 2 to 10 and further preferably 2 to 6 carbon atoms, and having further a carbonyl group bonded to an oxygen atom of the above alkoxy group, which is specifically exemplified by a methoxycarbonyl group, an ethoxycarbonyl group, a n-propoxycarbonyl group, a n-butoxycarbonyl group, a tert-butoxycarbonyl group, a pentyloxycarbonyl group, a sec-pentyloxycarbonyl group, a neopentyloxycarbonyl group, a hexyloxycarbonyl group, a cyclohexyloxycarbonyl group, a heptyloxycarbonyl group, a cycloheptyloxycarbonyl group, an octyloxycarbonyl group, a nonyloxycarbonyl group, a decyloxycarbonyl group, a cyclodecyloxycarbonyl group, an undecyloxycarbonyl group, a tetradecyloxycarbonyl group, a heptadecyloxycarbonyl group, a cycloheptadecyloxycarbonyl group, a nonadecyloxycarbonyl group, an icosyloxycarbonyl group, a cyclopentyloxycarbonyl group, a cyclohexyloxycarbonyl group, a cyclooctyloxycarbonyl group and a cycloheptadecyloxycarbbnyl group.

The aryloxycarbonyl group includes one generally having 7 to 15, preferably 7 to 11 carbon atoms, which is specifically exemplified by a phenyloxycarbonyl group, a naphthyloxycarbonyl group and an anthryloxycarbonyl group.

The alkoxysulfonyl group may be straight chained, branched or cyclic, and includes one generally having 2 to 21, preferably 2 to 15, more preferably 2 to 10 and further preferably 2 to 6 carbon atoms, having further a sulfonyl group bonded to an oxygen atom of the above alkoxy group, which is specifically exemplified by a methoxysulfonyl group, an ethoxysulfonyl group, a n-propoxysulfonyl group, a n-butoxysulfonyl group, a tert-butoxysulfonyl group, a pentyloxysulfonyl group, a sec-pentyloxysulfonyl group, a neopentyloxysulfonyl group, a hexyloxysulfonyl group, a cyclohexyloxysulfonyl group, a heptyloxysulfonyl group, a cycloheptyloxysulfonyl group, an octyloxysulfonyl group, a nonyloxysulfonyl group, a decyloxysulfonyl group, a cyclodecyloxysulfonyl group, an undecyloxysulfonyl group, a tetradecyloxysulfonyl group, a heptadecyloxysulfonyl group, a cycloheptadecyloxysulfonyl group, a nonadecyloxysulfonyl group, an icosyloxysulfonyl group, a cyclopentyloxysulfonyl group, a cyclohexyloxysulfonyl group, a cyclooctyloxysulfonyl group and a cycloheptadecyloxysulfonyl group.

The aryloxysulfonyl group includes one generally having 7 to 15, preferably 7 to 11 carbon atoms, which is specifically exemplified by a phenyloxysulfonyl group, a naphthyloxysulfonyl group and an anthryloxysulfonyl group.

The acyl group includes one derived from a carboxylic acid or a sulfonic acid, and an acyl group derived from a carboxylic acid includes one derived from an aliphatic carboxylic acid or an aromatic carboxylic acid. The acyl group derived from a sulfonic acid includes one derived from an aliphatic sulfonic acid or an aromatic sulfonic acid.

The acyl group derived from an aliphatic carboxylic acid may be straight chained, branched or cyclic, and may also have a double bond in the chain, and includes one generally having 2 to 20, preferably 2 to 15, more preferably 2 to 10 and further preferably 2 to 6 carbon atoms, which is specifically exemplified by an acetyl group, a propionyl group, a butyryl group, an isobutyryl group, a valeryl group, an isovaleryl group, a pivaloyl group, a hexanoyl group, a heptanoyl group, an octanoyl group, a decanoyl group, a lauroyl group, a myristoyl group, a palmitoyl group, a stearoyl group, an icosanoyl group, an acryloyl group, a methacryloyl group, a crotonoyl group and an oleoyl group. The acyl group derived from an aromatic carboxylic acid includes one generally having 7 to 15, preferably 7 to 11 carbon atoms, which is specifically exemplified by a benzoyl group, a naphthoyl group and an anthroyl group.

The acyl group derived from an aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfofnyl group, an isopropylsulfonyl group, a n-butylsulfonyl group, an isobutylsulfonyl group, a tert-butylsulfonyl group, a n-pentylsulfonyl group, a n-hexylsulfonyl group, a heptylsulfonyl group, an octylsulfonyl group, a decylsulfonyl group, a tridecylsulfonyl group, a hexadecylsulfonyl group, an icosylsulfonyl group, a cyclohexylsulfonyl group and a cyclodecylsulfonyl group. The acyl group derived from an aromatic sulfonic acid includes one generally having 6 to 14, preferably 6 to 10 carbon atoms, which is specifically exemplified by a phenylsulfonyl group, a naphthylsulfonyl group and an anthrylsulfonyl group.

The acyloxy group includes an acyloxy group derived from a carboxylic acid having an —O— bonded to the acyl group derived from the above carboxylic acid, and the acyloxy group derived from a sulfonic acid having an —O— bonded to the acyl group derived from the above sulfonic acid. The acyloxy group derived from the carboxylic acid includes an acyloxy group derived from an aliphatic carboxylic acid and an aromatic carboxylic acid. The acyloxy group derived from the sulfonic acid includes an acyloxy group derived from an aliphatic sulfonic acid and an aromatic sulfonic acid.

The acyloxy group derived from the aliphatic carboxylic acid may be straight chained, branched or cyclic and may have further a double bond in the chain, and includes one generally having 2 to 20, preferably 2 to 15, more preferably 2 to 10 and further preferably 2 to 6 carbon atoms, which is specifically exemplified by an acetyloxy group, a propionyloxy group, a butyryloxy group, an isobutytyloxy group, a valeryloxy group, an isovaleryloxy group, a pivaloyloxy group, a hexanoyloxy group, a heptanoyloxy group, an octanoyloxy group, a decanoyloxy group, a lauroyloxy group, a myristoyloxy group, a palmitoyloxy group, a stearoyloxy group, an icosanoyloxy group, an acryloyloxy group, a methacryloyl group, a crotonoyl group, an oleoyloxy group, a cyclohexanoyloxy group and a cyclodecanoyloxy group. The acyloxy group derived from the aromatic carboxylic acid includes one generally having 7 to 15, preferably 7 to 11 carbon atoms, which is specifically exemplified by a benzoyloxy group, a naphthoyloxy group and an anthroyloxy group.

The acyloxy group derived from the aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyloxy group, an ethylsulfonyloxy group, a n-propylsulfonyloxy group, an isopropylsulfonyloxy group, a n-butylsulfonyloxy group, an isobutylsulfonyloxy group, a tert-butylsulfonyloxy group, a n-pentylsulfonyloxy group, a n-hexylsulfonyloxy group, a heptylsulfonyloxy group, an octylsulfonyloxy group, a decylsulfonyloxy group, a tridecylsulfonyloxy group, a hexadecylsulfonyloxy group, an icosylsulfonyloxy group, a cyclopentylsulfonyloxy group and a cyclohexylsulfonyloxy group. The acyloxy group derived from the aromatic sulfonic acid includes one generally having 6 to 14, preferably 6 to 10 carbon atoms, which is specifically exemplified by a phenylsulfonyloxy group, a naphthylsulfonyloxy group and an anthrylsulfonyl group.

The halogen atom includes a chlorine atom, a bromine atom, a fluorine atom and an iodine atom, and among others, a chlorine atom is preferable.

The carboxyl group, the sulfo group, the sulfino group, the sulfeno group, the phosphino group and the phosphinoyl group include also one, wherein a hydrogen atom in these groups is replaced by an alkali metal atom such as sodium, potassium and lithium.

Among the above substituents of the compound having an aromatic ring, of the present invention, deuteration of the compound having a substituent such as an alkoxycarbonyl group, an aryloxycarbonyl group and a cyano group, which is labile to decomposition under acidic or basic condition, relevant to the present invention, cannot decompose these substituents.

The above substituent of an aromatic ring which may have a substituent, that is an alkyl group, an alkenyl group, an aryl group, an aralkyl group, an alkoxy group, an aryloxy group, an alkylthio group, an arylthio group, an alkylsulfonyl group, an arylsulfonyl group, an alkylsulfinyl group, an arylsulfinyl group, an alkylphosphino group, an arylphosphino group, an alkylphosphinoyl group, an arylphosphinoyl group, an alkylamino group, an arylamino group, an alkoxycarbonyl group, an aryloxycarbonyl group, an alkoxysulfonyl group, an aryloxysulfonyl group, an acyl group and an acyloxy group, may have, includes an alkyl group, an alkenyl group, an alkynyl group, an aryl group, a hydroxy group, an alkoxy group, an amino group, an alkylamino group, a mercapto group, an alkylthio group, an formyl group, an acyl group, a carboxyl group, an alkoxycarbonyl group, a carbamoyl group and an alkylcarbamoyl group, may have further a substituent, and there substituents may be present generally 1 to 6, preferably 1 to 4, more preferably 1 to 2 in the substituent of the aromatic ring.

The alkyl group, the alkenyl group, the aryl group, the alkoxy group, the alkylamino group, the alkylthio group, the acyl group, the carboxyl group and the alkoxycarbonyl group as the substituent of the aromatic ring which may have a substituent, relevant to the present invention, includes one the same as the substituent of the above aromatic ring which may have a substituent.

The alkynyl group as the substituent of the aromatic ring which may have a substituent, relevant to the present invention, may be straight chained, branched or cyclic, and includes one generally having 2 to 20, preferably 2 to 10 and more preferably 2 to 6 carbon atoms, wherein not less than one carbon-carbon triple bond is included in the chain of an alkyl group having not less than two carbon atoms, among the above alkyl groups, which is specifically exemplified by an ethenyl group, a 2-propynyl group, a 2-pentynyl group, a 2-nonyl-3-butynyl group, a cyclohexyl-3-ynyl group, a 4-octynyl group and 1-methyldecyl-5-ynyl group.

The alkylcarbamoyl group as the substituent of the aromatic ring which may have a substituent, relevant to the present invention, includes one, wherein one or two of hydrogen atoms of a carbamoyl group is independently replaced by the above alkyl group, which is specifically exemplified by a methylcarbamoyl group, an ethylcarbamoyl group, a n-propylcarbamoyl group, an isopropylcarbamoyl group, a n-butylcarbamoyl group, an isobutylcarbamoyl group, a tert-butylcarbamoyl group, a pentylcarbamoyl group, a hexylcarbamoyl group, a heptylcarbamoyl group, an octylcarbamoyl group, a nonylcarbamoyl group, a decylcarbamoyl group, a dodecylcarbamoyl group, a tetradecylcarbamoyl group, a pentadecylcarbamoyl group, a hexadecylcarbamoyl group, a heptadecylcarbamoyl group, a nonadecylcarbamoyl group, an icosylcarbamoyl group, a cyclopentylcarbamoyl group, a cyclohexylcarbamoyl group, a cycloheptylcarbamoyl group, a dimethylcarbamoyl group, an ethylmethylcarbamoyl group, a diethylcarbamoyl group, a methylpropylcarbamoyl group, a dipropylcarbamoyl group, an ethylhexylcarbamoyl group, a dibutylcarbamoyl group, a heptylmethylcarbamoyl group, a methyloctylcarbamoyl group, a decylmethylcarbamoyl group, a dodecylethylcarbamoyl group, a methylpentadecylcarbamoyl group, an ethyloctadecylcarbamoyl group, a cyclopentylmethylcarbamoyl group, a cyclohexylmethylcarbamoyl group, a cyclohexylethylcarbamoyl group, a cyclohexylpropylcarbamoyl group, a cyclohexylbutylcarbamoyl group and a dicyclohexylcarbamoyl group.

In a method for deuteration of the present invention, heavy hydrogen source to react with the above compound having an aromatic ring includes heavy hydrogen gas ($D_2$, $T_2$) and a deuterated solvent.

In case that a heavy hydrogen is deuterium, specific examples of a deuterated solvent as deuteration source include deuterium oxide ($D_2O$), deuterated alcohols such as deuterated methanol, deuterated ethanol, deuterated isopropanol, deuterated butanol, deuterated tert-butanol, deuterated pentanol, deuterated hexanol, deuterated heptanol, deuterated octanol, deuterated nonanol, deuterated decanol, deuterated undecanol and deuterated dodecanol, deuterated carboxylic acids such as deuterated formic acid, deuterated acetic acid, deuterated propionic acid, deuterated butyric acid, deuterated isobutyric acid, deuterated valeric acid, deuterate isovaleric acid and deuterated pivalic acid, deuterated ketones such as deuterated acetone, deuterated methyl ethyl ketone, deuterated methyl isobutyl ketone, deuterated diethyl ketone, deuterated diprdpyl ketone, deuterated diisopropyl ketone and deuterated dibutyl ketone, organic solvents such as deuterated dimethylsulfoxide, and among others, deuterium oxide and deuterated alcohols are preferable, and deuterium oxide and deuterated methanol are more preferable, and deuterium oxide is particularly preferable in view of environmental aspect and operability. In case that a heavy hydrogen is tritium, specific examples of a deuterated solvent as the deuteration source includes tritium oxide ($T_2O$) and the like.

The deuterated solvent may be one, wherein at least one hydrogen atom in the molecule is deuterated, and for example, deuterated alcohols wherein at least a hydrogen atom in a hydroxyl group is deuterated, or deuterated carboxylic acids wherein at least a hydrogen atom in a carboxyl group is deuterated, can be used in a method for deuteration of the present invention, and among others, a solvent wherein all hydrogen atoms in the molecule are deuterated is particularly preferable.

As an amount of heavy hydrogen source to be used is increasing, deuteration of the present invention tends to proceed further, however, in view of cost, the amount of heavy hydrogen source is the amount so that as lower limit, generally not less than equimolar, preferably in order, not less than 10 molar times, 20 molar times, 30 molar times and 40 molar times, and as upper limit, generally 250 molar times or less, preferably 150 molar times or less, of a heavy hydrogen atom is contained in heavy hydrogen source, relative to hydrogen atoms deuteratable in the compound having an aromatic ring as a reactive substrate.

In a method for deuteration of the present invention, a reaction solvent may be used if necessary. When a reaction substrate is liquid, use of the reaction solvent is not necessary even if heavy hydrogen gas is used as heavy hydrogen source, and even when a reaction substrate is solid, use of a reaction solvent is not required in particular, in case that a deuterated solvent is used as heavy hydrogen source. However, in case that a reaction substrate is solid and heavy hydrogen source is heavy hydrogen gas, use of a suitable reaction solvent is necessary.

A reaction solvent to be used if necessary is preferably one not deuterated by heavy hydrogen gas used as heavy hydrogen source, or such one as even when deuterated by heavy hydrogen gas, said deuterated reaction solvent can be used as it is as heavy hydrogen source for deuteration of the present invention. A reaction solvent which hardly dissolves a substrate can be used because a reaction system of deuteration of the present invention can be carried out in suspension state, however, one which easily dissolves a substrate is preferable.

When a solvent deuterated by heavy hydrogen gas as heavy hydrogen source cannot be used as heavy hydrogen source for deuteration of the present invention, use of such a solvent is not preferable as a reaction solvent, because most of heavy hydrogen gas as heavy hydrogen source are consumed for deuteration of the solvent and not for objective deuteration of the present invention.

The specific examples of the reaction solvent to be used if necessary, includes ethers such as dimethyl ether, diethyl ether, diisopropyl ether, ethylmethyl ether, tert-butylmethyl ether, 1,2-dimethoxyethane, oxirane, 1,4-dioxane, dihydropyran and tetrahydrofuran, organic solvents not deuteratable by heavy hydrogen gas such as aliphatic hydrocarbons including hexane, heptane, octane, nonane, decane and cyclohexane, water, alcohols such as methanol, ethanol, isopropanol, butanol, tert-butanol, pentanol, hexanol, heptanol, octanol, nonanol, decanol, undecanol and dodecanol, carboxylic acids such as formic acid, acetic acid, propionic acid, butyric acid, isobutyric acid, valeric acid, isovaleric acid and pivalic acid, ketones such as acetone, methyl ethyl ketone, methyl isobutyl ketone, diethyl ketone, dipropyl ketone, diisopropyl ketone and dibutyl ketone, organic solvents usable as heavy hydrogen source of the present invention even if deuterated by heavy hydrogen gas, such as dimethylsulfoxide.

The catalyst selected from an activated platinum catalyst, rhodium catalyst, ruthenium catalyst, nickel catalyst and cobalt catalyst in the present invention, (hereinafter may be abbreviated as an activated catalyst) means an ordinary platinum catalyst, rhodium catalyst, ruthenium catalyst, nickel catalyst or cobalt catalyst (hereinafter may be abbreviated as a "non-activated catalyst" or simply as a "catalyst") which is activated by contact with hydrogen gas or heavy hydrogen gas.

In a method for deuteration of the present invention, as an activated catalyst, a non-activated catalyst may be used by activation beforehand, or a non-activated catalyst itself may be used similarly, if hydrogen gas or heavy hydrogen gas is present in a reaction system.

In order for hydrogen gas or heavy hydrogen gas to be present in a reaction system, hydrogen gas or heavy hydrogen gas may directly be passed through a reaction solution, or a sealed reaction system for deuteration of the present invention may be replaced by hydrogen gas or heavy hydrogen gas.

As described above, activation of a catalyst by using a method for sealing a reaction system for deuteration of the present invention, and then replacing with hydrogen gas or heavy hydrogen gas, can provide deuteration of the present invention further efficiently due to no requirement of process that a catalyst is deuterated beforehand.

The platinum catalyst includes one having generally 0 to 4, preferably 0 to 2 and more preferably 0 valence of a platinum atom.

The rhodium catalyst includes one having generally 0 or 1, preferably 0 valence of a rhodium atom.

The ruthenium catalyst includes one having generally 0 to 2, preferably 0 valence of a ruthenium atom.

The nickel catalyst includes one having generally 0 to 2, preferably 0 valence of a nickel atom.

The cobalt catalyst includes one having generally 0 or 1, preferably 0 valence of a cobalt atom.

The above catalyst may be a metal catalyst consisting of platinum, rhodium, ruthenium, nickel or cobalt, which may have a ligand, or may be one consisting of these metals supported on various carriers.

Among catalysts in a method for deuteration of the present invention, the ligand of the metal catalyst which may have a ligand, includes 1,5-cyclooctadiene (COD), dibenzylideneacetone (DBA), tricyclohexylphosphine ($PCy_3$), triethoxyphosphine ($P(OEt)_3$), tri-tert-butylphosphine ($P(O^tBU)_3$), bipyridine (BPY), phenanthroline (PHE), triphenylphosphine ($PPh_3$), 1,2-bis(diphenylphosphino)ethane (DPPE), triphenoxyphosphine ($P(OPh)_3$) and trimethoxyphosphine ($P(OCH_3)_3$).

The platinum based metal catalyst includes, Pt, platinum catalysts such as $PtO_2$, $PtCl_4$, $PtCl_2$ and $K_2PtCl_4$, and platinum catalysts with a ligand such as $PtCl_2(cod)$, $PtCl_2(dba)$, $PtCl_2(PCy_3)_2$, $PtCl_2(P(OEt)_3)_2$, $PtCl_2(P(O^tBu)_3)_2$, $PtCl_2(bpy)$, $PtCl_2(phe)$, $Pt(PPh_3)_4$, $Pt(cod)_2$, $Pt(dba)_2$, $Pt(bpy)_2$, and $Pt(phe)_2$.

The rhodium based metal catalyst includes, Rh and rhodium catalysts with a ligand such as $RhCl(PPh_3)_3$.

The ruthenium based metal catalyst includes, Ru and ruthenium catalysts with a ligand such as $RuCl_2(PPh_3)_3$.

The nickel based metal catalyst includes, Ni, nickel catalysts such as $NiCl_2$ and NiO, and nickel catalysts with a ligand such as $NiCl_2(dppe)$, $NiCl_2(PPh_3)_2$, $Ni(PPh_3)_4$, $Ni(P(OPh)_3)_4$ and $Ni(cod)_2$.

The cobalt based metal catalyst includes, cobalt catalysts with a ligand such as $Co(C_3H_5)\{P(OCH_3)_3\}_3$.

The carrier, in the case that the above catalyst is supported on a carrier, includes carbon, alumina, silica gel, zeolite, molecular sieve, ion-exchange resins and polymers, and among others, carbon, alumina, silica gel, zeolite and molecular sieve are preferable, and carbon and alumina are particularly preferable.

The ion exchange resin used as a carrier may be one having no serious effect on deuteration of the present invention and includes a cation exchange resin and an anion exchange resin.

The cation exchange resin includes a weak acidic cation exchange resin and strong acidic cation exchange resin. The anion exchange resin includes a weak basic anion exchange resin and strong basic anion exchange resin.

The ion exchange resin generally contains a polymer cross-linked with a difunctional monomer as a skeleton polymer, to which an acidic group or a basic group is bonded and then is exchanged by various cations and anions (a counter ion), respectively.

The specific examples of the weak acidic cation exchange resin include one obtained by hydrolysis of a polymer of acrylate ester or a methacrylate ester, cross-linked by divinylbenzene.

The specific examples of the strong acidic cation exchange resin include one obtained by sulfonation of a copolymer of styrene-divinylbenzene.

The specific examples of the strong basic anion exchange resin include one wherein an amino group is bonded to an aromatic ring of a copolymer of stylene-divinylbenzene.

Strength of basicity of a basic anion exchange resin increases with an amino group bonded in the order of a primary amino group, a secondary amino group, a tertiary amino group, a quaternary ammonium salt.

An ion exchange resin generally available on the market may be used as much as the above ion exchange resin.

The polymer used as a carrier is not specifically limited unless it has serious effect on deuteration of the present invention, however, an example of such a polymer includes one obtained by polymerization or copolymerization of a monomer shown by the following general formula [1]:

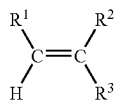

[1]

(wherein $R^1$ is a hydrogen atom, a lower alkyl group, a carboxyl group, a carboxyalkyl group, an alkoxycarbonyl group, a hydroxyalkoxycarbonyl group, a cyano group or a formyl group, $R^2$ is a hydrogen atom, a lower alkyl group, a carboxyl group, an alkoxycarbonyl group, a hydroxyalkoxycarbonyl group, a cyano group or a halogen atom, $R^3$ is a hydrogen atom, a lower alkyl group, a haloalkyl group, a hydroxyl group, an aryl group which may have a substituent, an aliphatic heterocyclic group, an aromatic heterocyclic group, a halogen atom, an alkoxycarbonyl group, a hydroxyalkoxycarbonyl group, a sulfo group, a cyano group, a cyano-containing alkyl group, an acyloxy group, a carboxyl group, a carboxyalkyl group, an aldehyde group, an amino group, an aminoalkyl group, a carbamoyl group, a N-alkylcarbamoyl group, a hydroxyalkyl group, and $R^2$ and $R^3$ may form an alicyclic ring together with the adjacent —C=C— bond).

In the general formula [1], the lower alkyl group shown by $R^1$ to $R^3$ may be straight chained, branched or cyclic, and includes an alkyl group having 1 to 6 carbon atoms, which is specifically exemplified by a methyl group, an ethyl group, a n-propyl group, an isopropyl group, a n-butyl group, an isobutyl group, a tert-butyl group, a sec-butyl group, a n-pentyl group, an isopentyl group, a tert-pentyl group, a 1-methylpentyl group, a n-hexyl group, an isohexyl group, a cyclopropyl group, a cyclopentyl group and a cyclohexyl group.

The carboxyalkyl group shown by $R^1$ and $R^2$ includes one, wherein a part of hydrogen atoms of the above lower alkyl group is replaced by a carboxyl group, which is specifically exemplified by a carboxymethyl group, a carboxyethyl group, a carboxypropyl group, a carboxybutyl group, a carboxypentyl group and a carboxyhexyl group.

The alkoxycarbonyl group shown by $R^1$ to $R^3$ includes preferably one having 2 to 11 carbon atoms, which is specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group and a decyloxycarbonyl group.

The hydroxyalkoxycarbonyl group shown by $R^1$ and $R^3$ includes one, wherein a part of hydrogen atoms of the above alkoxycarbonyl group having 2 to 11 carbon atoms is replaced by a hydroxyl group, which is specifically exemplified by a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group and a hydroxydecyloxycarbonyl group.

The halogen atom shown by $R^2$ and $R^3$ includes fluorine, chlorine bromine and iodine.

The haloalkyl group shown by $R^3$ includes one having 1 to 6 carbon atoms, wherein the above lower alkyl group shown by $R^1$ to $R^3$ is halogenated (for example, fluorinated, chlorinated, brominated, iodinated, etc.), which is specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group and a 6-chlorohexyl group.

The aryl group of the aryl group which may have a substituent includes a phenyl group, a tolyl group, a xylyl group and a naphthyl group, and said substituent includes an amino group, a hydroxyl group, a lower alkoxy group and a carboxyl group. The specific examples of the substituted aryl group include an aminophenyl group, a toluidino group, a hydroxyphenyl group, a methoxyphenyl group, a tert-butoxyphenyl group and a carboxyphenyl group.

The aliphatic heterocyclic group includes preferably a 5- or 6-membered one having 1 to 3 hetero atoms such as a nitrogen atom, an oxygen atom and a sulfur atom, which is specifically exemplified by a 2-oxopyrrolidyl group, a piperidyl group, a piperidino group, a piperazinyl group and a morpholino group.

The aromatic heterocyclic group includes preferably a 5- or 6-membered one having 1 to 3 hetero atoms such as a nitrogen atom, an oxygen atom and a sulfur atom, which is specifically exemplified by a pyridyl group, an imidazolyl group, a thiazolyl group, a furyl group and a pyranyl group.

The cyano-containing alkyl group includes one, wherein a part of hydrogen atoms of the above lower alkyl group is replaced by a cyano group, which is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group and a 6-cyanohexyl group.

The acyloxy group includes one derived from a carboxylic acid having 2 to 20 carbon atoms, which is specifically exemplified by an acetyloxy group, a propionyloxy group, a butyryloxy group, a pentanoyloxy group, a nonanoyloxy group, a decanoyloxy group and a benzoyloxy group.

The aminoalkyl group includes one, wherein a part of hydrogen atoms of the above lower alkyl group is replaced by an amino group, which is specifically exemplified by an aminomethyl group, an aminoethyl group, an aminopropyl group, an aminombutyl group, an aminopentyl group and an aminohexyl group.

The N-alkylcarbamoyl group includes one, wherein a part of hydrogen atoms of a carbamoyl group is replaced by an alkyl group, which is specifically exemplified by an N-methylcarbamoyl group, an N-ethylcarbamoyl group, an N-n-propylcarbamoyl group, an N-isopropylcarbamoyl group, an N-n-butylcarbamoyl group and an N-tert-butylcarbamoyl group.

The hydroxyalkyl group includes one, wherein a part of hydrogen atoms of the above lower alkyl group is replaced by a hydroxyl group, which is specifically exemplified by a hydroxymethyl group, a hydroxyethyl group, a hydroxypropyl group, a hydroxybutyl group, a hydroxypentyl group and a hydroxyhexyl group.

The aliphatic ring in the case where $R^2$ and $R^4$ are bonded together with the adjacent —C=C— bond to form alicyclic ring, includes an unsaturated alicyclic ring having 5 to 10 carbon atoms, and may be monocyclic or polycyclic, which is specifically exemplified by a norbornene ring, a cyclopentene ring, a cyclohexene ring, a cyclooctene ring and a cyclodecene ring.

The specific examples of the monomer shown by the general formula [1] include ethylenically unsaturated aliphatic hydrocarbons having 2 to 20 carbon atoms such as ethylene, propylene, butylene and isobutylene, ethylenically unsaturated aromatic hydrocarbons having 8 to 20 carbon atoms such as styrene, 4-methylstyrene, 4-ethylstyrene and divinylbenzene, alkenyl esters having 3 to 20 carbon atoms such as vinyl formate, vinyl acetate, vinyl propionate and isopropenyl acetate, halogen containing ethylenically unsaturated compounds having 2 to 20 carbon atoms such as vinyl chloride, vinylidene chloride, vinylidene fluoride and tetrafluoroethylene, ethylenically unsaturated carboxylic acids having 3 to 20 carbon atoms such as acrylic acid, methacrylic acid, itaconic acid, maleic acid, fumaric acid, crotonic acid, vinylacetic acid, allylacetic acid and vinylbenzoic acid, (these acids may form an alkaline metal such salt as sodium and potassium, or ammonium salts), ethylenically unsaturated carboxylic acid esters such as methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate, cyano containing ethylenically unsaturated compounds having 3 to 20 carbon atoms such as acrylonitrile, methacrylonitrile and allyl cyanide, ethylenically unsaturated amide compounds having 3 to 20 carbon atoms such as acrylamide and methacrylamide, ethylenically unsaturated aldehydes having 3 to 20 carbon atoms such as acrolein and crotonaldehyde, ethylenically unsaturated sulfonic acids having 2 to 20 carbon atoms such as vinylsulfonic acid and 4-vinylbenzene sulfonic acid, (these acids may form an alkaline metal salts such as sodium and potassium), ethylenically unsaturated aliphatic amines having 2 to 20 carbon atoms such as vinylamine and allylamine, ethylenic unsaturated aromatic amines having 8 to 20 carbon atoms such as vinylaniline, ethylenically unsaturated aliphatic heterocyclic amines having 5 to 20 carbon atoms such as N-vinylpyrrolidone and vinylpiperidine, ethylenically unsaturated alcohols having 3 to 20 carbon atoms such as allyl alcohol and crotyl alcohol, ethylenically unsaturated phenols having 8 to 20 carbon atoms such as 4-vinylphenol, and the like.

When the above polymer is used as a carrier, use of the carrier that is hard to be deuterated itself by deuteration of the present invention is preferable, however, an catalyst supported on the carrier deuteratable itself can be also used for deuteration of the present invention.

In the method for deuteration of the present invention among the above catalysts, a platinum-based catalyst and a rhodium-based catalyst are preferably used, and particularly a platinum-based catalyst is preferably used.

An amount of the activated catalyst or non-activated catalyst to be used is the amount so that generally catalyst quantity, preferably 0.01 to 50% by weight, more preferably 0.01 to 20% by weight and further more preferably 0.1 to 20% by weight, relative to the compound having an aromatic ring used as a reaction substrate.

In case where a non-activated catalyst is used in the reaction of the present invention, an amount of the hydrogens used when making the hydrogen exist in a reaction system in order to activate the non-activated catalyst is generally 1 to 20,000 equivalents and preferably 10 to 700 equivalents, relative to the catalyst, because excessive amount of hydrogen has adverse effect on a deuteration reaction of the present invention, such as hydrogenation of a deuterated solvent as heavy hydrogen source and decrease of rate of a heavy hydrogen as heavy hydrogen source in the reaction system.

An amount of heavy hydrogens used when making the heavy hydrogens exist in a reaction system in order to activate the non-activated catalyst may be sufficient amount to activate the catalyst, generally 1 to 20,000 equivalents and preferably 10 to 700 equivalents, relative to the catalyst, however, even if the amount of the said heavy hydrogen is large, deuteration of the present invention can be performed without any problem, because said heavy hydrogen can be also used as heavy hydrogen source of the present invention.

The lower limit of reaction temperature in a method for deuteration of the present invention is generally not less than 10° C., and preferably in order, not less than 20° C., 40° C., 60° C., 80° C., 140° C. and 160° C., higher temperature being more preferable, and the upper limit thereof is generally 300° C. or less, and preferably in order 200° C. or less and 180° C. or less, the latter being more preferable.

A reaction time in a method for deuteration of the present invention is generally 30 minutes to 72 hours and preferably 3 to 30 hours.

A method for deuteration of the present invention will be specifically explained by taking, as an example, the case of using heavy water as heavy hydrogen source and using a platinum carbon (Pt: 5%) as a non-activated catalyst.

For example, 500 mg of a compound having an aromatic ring (substrate) and 100 mg of a non-activated catalyst are added to 17 mL of a deuterated solvent, followed by replacing an atmosphere of a sealed reaction system with hydrogen and reacting with stirring in an oil bath at about 80° C. for about 24 hours. After completion of the reaction, when the reaction product is soluble in a deuterated solvent, the catalyst is filtered out from the reaction solution, and the filtrate is subjected to as it is structural analysis by $^1$H-NMR, $^2$H-NMR and mass spectrum measurement. When the reaction product is hardly soluble in the deuterated solvent, the reaction product is isolated from the reaction solution to be subjected to structural analysis by $^1$H-NMR, $^2$H-NMR and mass spectrum measurement.

When the product is hardly soluble in a deuterated solvent, the isolation of the product from the reaction solution may be carried out according to known purification methods such as extraction of the product from the reaction solution using an organic solvent and the like in which the product is soluble and then filtering out the catalyst.

Even when a compound having an aromatic ring contains a halogen atom as a substituent, only the aromatic ring can be deuterated without the above halogen atom being substituted by a hydrogen atom or a deuterium atom, or even when the compound having an aromatic ring contains a substituent such as a nitro group and a cyano group, only the aromatic ring can be deuterated without the above substitutes being reduced, by performing a method for deuteration of the present invention using a catalyst activated in advance as an activated catalyst and a deuterated solvent as heavy hydrogen source.

Further, in a method for deuteration of the present invention, a hydrogen atom other than a hydrogen atom belonging to an aromatic ring of a compound having the aromatic ring can be also deuterated.

As described above, a method for deuteration of the present invention that a compound having an aromatic ring is reacted with heavy hydrogen source in the presence of an activated catalyst, can efficiently deuterate (to replace with deuterium and tritium) a hydrogen atom belonging to an aromatic ring of a compound having the aromatic ring.

Because a method for deuteration of the present invention can be performed in a neutral condition even under relatively lower temperature condition, that is room temperature to about 160° C., than that in a conventional method thereof, it can not only improve a working environment but also be applied to deuteration of a substrate that is labile to decomposition under high temperature, of acid-base condition.

Further, a method for deuteration of the present invention can deuterate a substrate directly without use of a step of once introducing a substituent such as a halogen atom before deuteration.

Still further, a method for deuteration of the present invention can deuterate a compound having a halogen atom directly bonded to an aromatic ring thereof, with leaving the halogen atom as it is, which was difficult with a conventional method.

In addition, among the compounds obtained by the above method for deuteration of the present invention, a compound represented by the following general formula [2]:

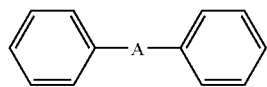

[2]

(wherein A is a sulfur atom, a sulfinyl group or a sulfonyl group and at least one of hydrogen atoms belonging to an aromatic ring is a heavy hydrogen atom), is extremely useful as a dopant for an optical fiber and the like.

In compounds represented by the above formula [2], diphenylsulfide wherein A is a sulfur atom, and diphenylsulfoxide wherein A is a sulfinyl group can also be obtained by, for example, a method shown below, other than the above method for deuteration of the present invention.

Deuterated diphenylsulfone prepared by a method for deuteration of the present invention is reduced using a reducing agent such as aluminum lithium hydride and the like according to a method described in J. Am. Chem. Soc. 1965, 87, 5614 and J. Am. Chem. Soc. 1966, 88, 1458 and the like to obtain deuterated diphenylsulfide and then the deuterated diphenylsulfide is oxidized using an oxidizing agent such as hydrogen peroxide and the like to obtain deuterated diphenylsulfoxide.

Average ratio of heavy hydrogen atoms to hydrogen atoms belonging to a compound represented by the general formula [2] of the present invention (deuteration ratio) is generally not lower than 5%, and preferably in order, not lower than 10%, 20%, 40%, 50% and 60%, wherein higher % is more preferable, and deuteration ratio at the meta position and/or the para position of an aromatic ring of said compound is generally not lower than 5%, and preferably in order, not lower than 40%, 50%, 60%, 70% and 80%, wherein higher % is more preferable.

In the following, The present invention is explained in further detail referring to Examples, but the present invention is not limited thereto by any means.

EXAMPLE

Example 1

In 17 mL of deuterium oxide ($D_2O$) were suspended 500 mg of phenol and 100 mg of platinum carbon (Pt 5%), followed by replacing the atmosphere of a sealed reaction system with hydrogen gas and conducting a reaction in an oil bath at 160° C. for about 24 hours. After completion of the reaction, the reaction solution was extracted with ether, followed by filtering out the catalyst and concentration of the filtrate under reduced pressure to be subjected to structural analysis by $^1$H-NMR, $^2$H-NMR and mass spectrum measurement. Deuteration ratio of the substrate turned out to be 98%. The result is shown in Table 1.

Examples 2 to 16

The same reaction and structural analysis as in Example 1 was conducted, except for using 500 mg of a substrate and 100 mg of a catalyst (provided 10 mg in the case of $K_2PtCl_4$ catalyst) at reaction temperature condition as shown in Table 1. Deuteration ratios of obtained substrates are also shown in Table 1. In Table 1, "Pt/C" shows platinum carbon (Pt 5%); "$K_2PtCl_4$" shows platinous (II) potassium chloride; "o-, p- and m-" of deuteration ratios show deuteration ratios at ortho, para and meta position of an aromatic ring, respectively; and "2,4-, 5- and 6-" of deuteration ratios of m-chlorophenol in Examples 5 and 6 show deuteration ratios of a hydrogen atom located as shown in the following formula below, providing that "2,4-" shows average deuteration ratio of hydrogen atoms at both location; and deuteration ratio in Example 16 shows deuteration ratio of a hydrogen atom belonging to an aromatic ring.

TABLE 1

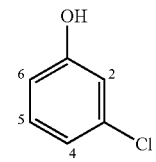

| Substrate | Catalyst | Reaction Temp. (° C.) | Deuteration Ratio (%) |
|---|---|---|---|
| Exp.1 | phenol | Pt/C | 160 | 98 |
| Exp.2 | diphenyl-methane | Pt/C | room temp. | 65 |
| Exp.3 | diphenyl-methane | Pt/C | 80 | 96 |
| Exp.4 | diphenyl-methane | $K_2PtCl_4$ | 160 | 81 |
| Exp.5 | m-chloro-phenol | Pt/C | 160 | 2,4-59, 5-58, 6-83 |
| Exp.6 | m-chloro-phenol | Pt/C | 180 | 2,4-71, 5-70, 6-98 |
| Exp.7 | aniline | Pt/C | 80 | 98 |
| Exp.8 | aniline | Pt/C | 160 | 99 |
| Exp.9 | benzoic acid | Pt/C | 80 | p-96, m-96, o-50 |
| Exp.10 | benzoic acid | Pt/C | 160 | 99 |
| Exp.11 | sodium | Pt/C | 80 | p-92, m-79, o-52 |

TABLE 1-continued

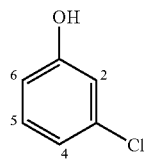

| | Substrate | Catalyst | Reaction Temp. (° C.) | Deuteration Ratio (%) |
|---|---|---|---|---|
| Exp.12 | benzoate sodium benzoate | Pt/C | 160 | 99 |
| Exp.13 | diphenyl-sulfone | Pt/C | 160 | p-64, m-52, o-0 |
| Exp.14 | diphenyl-sulfone | Pt/C | 180 | p-88, m-79, o-7 |
| Exp.15 | o-phenylene-diamine | Pt/C | 180 | 98 |
| Exp.16 | 4-methoxy-1,2-phenyl-enediamine | Pt/C | 180 | 98 |

Comparative Example 1

In 16 mL of deuterium oxide ($D_2O$) were added 500 mg of diphenylmethane and 0.7 mL of hydrochloric acid, followed by replacing the atmosphere of a sealed reaction system with nitrogen and conducting a reaction while stirring at 80° C. for 24 hours. After completion of the reaction, the reaction solution was extracted with diethyl ether, followed by washing of an obtained organic layer with water and concentration under reduced pressure to be subjected to structural analysis by $^1$H-NMR, $^2$H-NMR and mass spectrum measurement. Deuteration ratio of the substrate turned out to be 0%.

Comparative Example 2

In 16 mL of deuterium oxide ($D_2O$) were added 500 mg of phenol and 0.7 mL of hydrochloric acid, followed by replacing the atmosphere of a sealed reaction system with nitrogen and conducting a reaction with stirring at 80° C. for 24 hours. After completion of the reaction, the reaction solution was extracted with diethyl ether, followed by washing of an obtained organic layer with water and concentration under reduced pressure to be subjected to structural analysis by $^1$H-NMR, $^2$H-NMR and mass spectrum measurement. Deuteration ratio of the substrate turned out to be 93%, 0% and 96% at para, meta and ortho positions, respectively.

Comparative Example 3

In 16 mL of deuterium oxide ($D_2O$) were added 500 mg of aniline and 0.7 mL of hydrochloric acid, followed by replacing the atmosphere of a sealed reaction system with nitrogen and conduction a reaction with stirring at 80° C. for 24 hours. After completion of the reaction, the reaction solution was neutralized with a 25% aqueous solution of sodium hydride, followed by extraction with diethyl ether, washing of an obtained organic layer with water and concentration under reduced pressure to be subjected to structural analysis by $^1$H-NMR, $^2$H-NMR and mass spectrum measurement. Deuteration ratio of the substrate turned out to be 12%, 0% and 12% at para, meta and ortho positions, respectively.

Comparative Example 4

In 16 mL of deuterium oxide ($D_2O$) were added 500 mg of benzoic acid and 0.7 mL of hydrochloric acid, followed by replacing the atmosphere of a sealed reaction system with by nitrogen and conducting to reaction with stirring at 80° C. for 24 hours. After completion of the reaction, the reaction solution was extracted with diethyl ether, followed by washing of an obtained organic layer with water and concentration under reduced pressure to be subjected to structural analysis by $^1$H-NMR, $^2$H-NMR and mass spectrum measurement. Deuteration ratio of the substrate turned out to be 0%.

It is clear from the results of Example 2 that even an aromatic ring of an aromatic compound having no hydrophilic functional group can be deuterated efficiently under comparably low temperature condition such as about room temperature, by a method for deuteration of the present invention.

Further, as is clear from comparison of Examples 5 to 9 and Comparative Examples 1 to 4, an aromatic ring can be deuterated efficiently without acidifying a reaction solution, by a method for deuteration of the present invention.

Furthermore, it is clear from the results of Examples 5 and 6 that a compound having a halogen atom directly bonded to an aromatic ring thereof can be deuterated, leaving the halogen atom as it is, by a method for deuteration of the present invention.

INDUSTRIAL APPLICABILITY

In accordance with a method for deuteration (replacement by deuterium and tritium) of the present invention, which comprises reacting the compound having an aromatic ring with heavy hydrogen source in the presence of an activated catalyst, a deuteration reaction which was conventionally possible only under severe conditions such as at high temperature, or under acid-base condition, can be attained under comparatively low temperature and neutral condition and thus work environment is remarkably improved.

Further, a method for deuteration of the present invention can be applied widely to deuteration of various compounds having an aromatic ring which are liable to decomposition under high temperature or acid-base condition, leading to industrial and efficient deuteration of a compound having an aromatic ring.

Furthermore, a method for deuteration of the present invention can not only provide deuteration of a substrate directly without using a step such as once introducing a substituent, for example, a halogen atom but also provide deuteration reaction of a compound having a halogen atom directly bonded to the aromatic ring thereof, leaving the halogen atom as it is which were difficult by conventional methods.

What is claimed is:

1. A method for deuteration of an aromatic ring comprising:

reacting the aromatic ring under a neutral condition with a deuterated solvent that is neither deuterium peroxide ($D_2O_2$) nor supercritical $D_2O$ in the presence of only one activated catalyst under non-supercritical condition, wherein the aromatic ring may have at least one substituent and is at least one selected from the group consisting of benzene, naphthalene, anthracene, phenanthrene, 9,10-dihydroanthracene, naphthacene, pentaphene, pentacene, hexaphene, hexacene, heptaphene, heptacene, trinaphthylene, 1,4-dihydronaphthalene, pyrene, triphenylene, biphenylene, indene, indan, indacene, phenalene, fluorene, acenaphthene, acenaphthylene, fluoranthene, tetraphenylene, coranthrene, acephenanthrylene, aceanthrylene, cyclopentaphenanthrene, chrysene, picene, pleiadene, rubicene, pyranthrene, coronene, perylene, rubrene, dibenzophenanthrene, 1,2-dibenzo-1,3-cycloheptadiene and ovalene, the reaction is carried out at 180° C. or lower, and the only one activated catalyst is activated platinum carbon and is activated with hydrogen or heavy hydrogen gas.

2. The method for deuteration according to claim 1, wherein the activated platinum carbon catalyst is one comprising platinum with valence of 0 to 2.

3. The method for deuteration according to claim 1, wherein the at least one substituent of the aromatic ring is selected from the group consisting of a halogen atom, a hydroxyl group, a mercapto group, an oxo group, a thioxo group, a carboxyl group, a sulfo group, a sulfino group, a sulfeno group, a phosphino group, a phosphinoyl group, a formyl group, an amino group, a cyano group and a nitro group.

4. The method for deuteration according to claim 1, wherein the at least one substituent of the aromatic ring is selected from the group consisting of an alkyl group, an alkenyl group, an aryl group, an aralkyl group, an alkoxy group, an aryloxy group, an alkylthio group, an arylthio group, an alkylsulfonyl group, an arylsulfonyl group, an alkylsulfinyl group, an arylsulfinyl group, an alkylphosphino group, an arylphosphino group, an alkylphosphinoyl group, an arylphosphinoyl group, an alkylamino group, an arylamino group, an alkoxycarbonyl group, an aryloxycarbonyl group, an alkoxysulfonyl group, an aryloxysulfonyl group, an acyl group and an acyloxy group, which may further have at least one substituent.

5. The method for deuteration according to claim 4, wherein the at least one substituent of the aromatic ring has at least one substituent selected from the group consisting of an alkyl group, an alkenyl group, an alkynyl group, an aryl group, a hydroxy group, an alkoxy group, an amino group, an alkylamino group, a mercapto group, an alkylthio group, an formyl group, an acyl group, a carboxyl group, an alkoxycarbonyl group, a carbamoyl group and an alkylcarbamoyl group.

6. The method for deuteration according to claim 1, where the deuterated solvent is at least one selected from the group consisting of deuterium oxide, deuterated alcohols, deuterated carboxylic acids, deuterated ketones, deuterated dimethylsulfoxide, and tritium oxide.

* * * * *